United States Patent [19]

Paul

[11] 4,158,015
[45] Jun. 12, 1979

[54] PROCESS FOR THE STEREOSELECTIVE SYNTHESIS OF THE E ISOMER OF ARYL ALKYL OXIMES

[75] Inventor: Jill H. Paul, Edgewater, N.J.

[73] Assignee: Mobil Oil Corporation, New York, N.Y.

[21] Appl. No.: 934,142

[22] Filed: Aug. 16, 1978

[51] Int. Cl.$^2$ ............................................ C07C 129/00
[52] U.S. Cl. ..................... 260/566 A; 260/340.5 R; 260/340.3; 260/465 E; 560/35; 560/18; 260/332.2 A; 260/332.3 R; 260/332.3 H; 260/329 R; 260/329 S; 260/329 HS; 260/329 AM; 260/330.5; 260/347.2; 260/346.22; 260/347.4; 260/347.7
[58] Field of Search ............ 260/566 A, 340.5, 340.3, 260/465 E, 332.2 A, 332.3 R, 332.3 H, 329 R, 329 S, 329 HS, 329 AM, 330.5, 347.2, 346.22, 347.4, 347.7; 560/35, 18

[56] References Cited

PUBLICATIONS

Ann., vol. 260, p. 63, (1890).
Journal of Organic Chemistry, vol. 20, p. 1491, (1955).
Journal of Medicinal Chemistry, vol. 20, (No. 9), p. 1199, (1977).

Primary Examiner—Gerald A. Schwartz
Attorney, Agent, or Firm—Charles A. Huggett; Hastings S. Trigg

[57] ABSTRACT

Mixtures of the E and Z isomers of aryl alkyl oximes are converted to 98% or greater E isomer by a process comprising treating a solution of a mixture of E and Z isomers in an organic solvent with a protic or Lewis acid, under anhydrous conditions, to precipitate >98% pure E isomer of an immonium complex and treating (neutralizing) the precipitate with an excess of dilute organic/inorganic base, such as $Na_2CO_3$ or $NaHCO_3$. The E isomer of the ketoxime is a precursor for highly insecticidal ketoximinoethers.

7 Claims, No Drawings

PROCESS FOR THE STEREOSELECTIVE SYNTHESIS OF THE E ISOMER OF ARYL ALKYL OXIMES

BACKGROUND OF THE INVENTION

1. Field of the Invention

This invention is concerned with a process of converting mixtures of E and Z isomers of certain ketoximes to >98% pure E isomer.

2. Description of the Prior Art

The isomerization of E aromatic aldoximes to Z aldoximes via the hydrochloride salt has been described in Ann. 260, 63 (1890). For example, the E isomer of p-chlorobenzaldoxime (I) was converted to the Z isomer (III) by saturating an ether solution of the E aldoxime with dry HCl and treating the resultant precipitate with sodium carbonate:

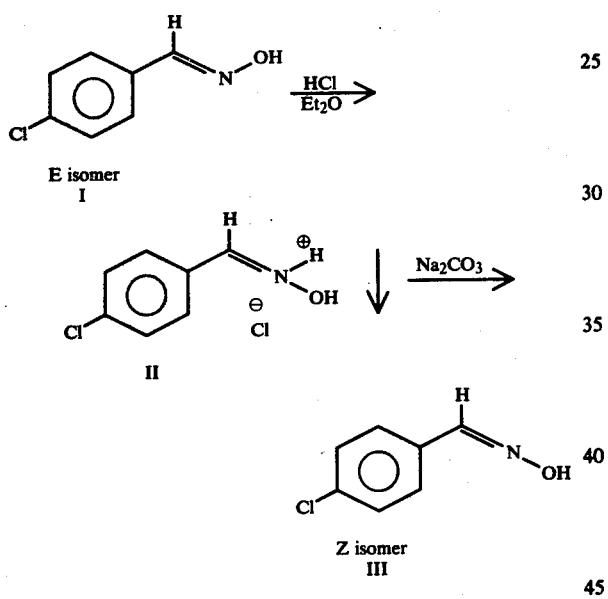

Hauser and Hoffenberg have reported, in J.O.C. 20, 1491 (1955), such isomerization utilizing the Lewis acid, BF₃. A benzene solution of the E isomer of p-chlorobenzaldoxime (I) with BF₃ to form a BF₃ complex (IV) and treating with NaHCO₃ solution to obtain the Z isomer (V).

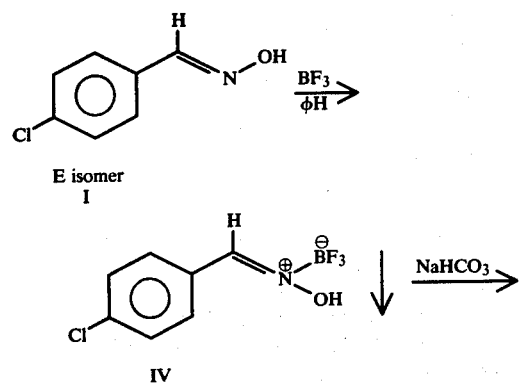

(2)

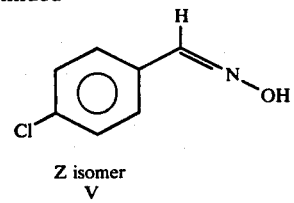

As reported in J. Med. Chem. 20, #9, 1199, (1977) the E isomer of an oximinoether (VI) in diethyl ether was treated with anhydrous HCl. A precipitate was isolated and suspended in water and extracted with ether to yield 37% of the Z isomer VII

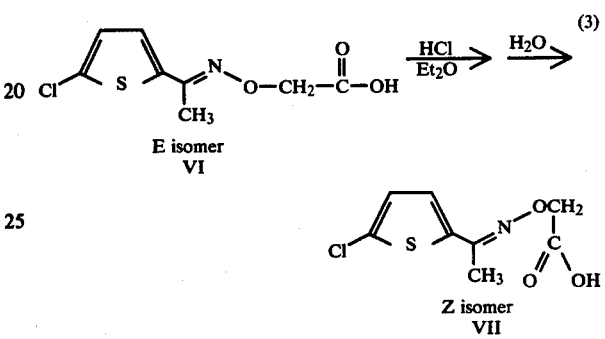

(3)

It is the surprising discovery of this invention that, contrary to the teaching of the prior art, mixtures of the E and Z isomers of aryl alkyl ketoximes, as contrasted to aldoximes, are converted to 98% E isomer.

SUMMARY OF THE INVENTION

This invention provides a process for producing >98% pure E isomer of an aryl alkyl ketoxime having the formula:

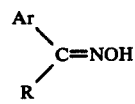

wherein Ar is phenyl; phenyl substituted in the 2- to 6-position with 1-5 halogen (Cl, Br, F, I), $C_1$–$C_4$ alkyl, $C_1$–$C_4$ alkoxy, $C_1$–$C_4$ alkylthio, methylenedioxy, ethylenedioxy, isopropylenedioxy, trifluoromethyl, $C_1$–$C_4$ haloalkyl, $C_1$–$C_4$ alkylthioalkyl, $C_2$–$C_4$ alkenyl, $C_2$–$C_4$ alkynyl, cyano, $C_2$–$C_4$ cyanoalkyl, $C_2$–$C_4$ carboalkoxy, $C_1$–$C_4$ alkylsulfonyl, $C_2$–$C_8$ alkoxyalkyl, $C_2$–$C_4$ haloalkenyl, or $C_1$–$C_4$ acyl; indanyl; naphthyl; benzofuryl; benzodihydrofuryl; benzothienyl; thienyl; R is $C_2$–$C_6$ alkyl, $C_3$–$C_6$ cycloalkyl, or $C_2$–$C_6$ alkenyl any of which can be substituted by halogen, hydroxy, $C_1$–$C_4$ alkoxy, $C_1$–$C_4$ alkylsulfonyl, cyano, nitro, $C_2$–$C_4$ carboalkoxy, or $C_1$–$C_4$ acyl; that comprises contacting a solution of mixed E and Z isomers of said aryl alkyl ketoxime in an anhydrous organic solvent with at least a stoichiometric amount of anhydrous protic or Lewis acid at between about −20° C. and about 150° C., thereby precipitating the E isomer of an immonium complex of said aryl alkyl ketoxime, separating said precipitate, neutralizing said precipitate with an excess of dilute aqueous $Na_2CO_3$ or $NaHCO_3$, and separating said E isomer.

DESCRIPTION OF SPECIFIC EMBODIMENTS

In addition to the ketoximes set forth in the specific examples, non-limiting examples of aryl alkyl ketoximes treated in accordance with this invention include:
p-trifluoromethylisobutyrophenone oxime;
p-methylthioisobutyrophenone oxime;
3,4-methylenedioxy phenyl propiophenone;
2,4-dichloroisobutyrophenone oxime;
p-cyanoisobutyrophenone oxime;
4-(d,α-dichloroethenyl)isobutyrophenone oxime;
p-ethynylisobutyrophenone oxime;
m-carbomethoxyisobutyrophenone oxime;
p-methylsulfonylpropiophenone oxime;
p-chloromethylpropiophenone oxime
2-(5-nitrothienyl) isopropyl ketoxime;
2-(4-chloro-5-bromomethylthienyl) isopropyl ketoxime;
2-(5-ethoxythienyl) isopropyl ketoxime;
2-(4-chlorothienyl) isopropyl ketoxime;
4-chlorophenyl cyclobutyl ketoxime;
4-chlorophenyl cyclohexyl ketoxime;
3,4,5-trichloroisobutyrophenone oxime;
3,4-dichloroisobutyrophenone oxime;
2,4,5-trichloroisobutyrophenone oxime;
3-chloro-4-bromoisobutyrophenone oxime;
4-benzothienyl isopropyl ketoxime.

In accordance with this invention, mixtures of E and Z isomers of the aryl alkyl ketoximes are precipitated as the E isomer immonium complex by treating a solution of the mixture in an anhydrous solvent with anhydrous protic or Lewis acids. It has been found that, unexpectedly, the E isomer in the mixture is precipitated as an immonium salt and the Z isomer isomerizes to the E isomer. Upon neutralization about 98% of the original mixture of isomers is recovered in the form of E isomer.

The organic solvent used can be any of the well known solvents used in organic synthesis operations, so long as the solvent is anhydrous. Typical utilizable anhydrous organic solvents include hydrocarbons, such as hexane, cyclohexane, toluene, and xylene; chlorinated hydrocarbons, such as chloroform and carbon tetrachloride; ethers, such as diethyl ether, tetrahydrofuran and dioxane; and ketones, such as acetone and 2-butanone. The amount of solvent used is not a critical factor, as it simply serves as a medium for the acid treatment. In general, between about one part and about 10 parts solvent per part aryl alkyl ketoxime can be used.

The acid used to precipitate the immonium salt of the aryl alkyl ketoxime will be an anhydrous organic or inorganic protic or Lewis acid. Typical acids include Lewis acids, such as boron trifluoride and aluminum chloride; mineral acids, such as sulfuric acid, orthophosphoric acid and polyphosphoric acids; hydrogen halide acids, such as hydrobromic acid and hydrochloric acid. HCl and BF$_3$ are preferred because they are gases and easily handled. At least a stoichiometric amount of the acid must be used, although an excess over the stoichiometric up to the point of saturation of the ketoxime solution is not detrimental.

The reaction of the aryl alkyl ketoxime with the acid to form the immonium complex or salt can be carried out at temperatures between about −20° C. and about 150° C., although temperatures between about 10° C. and about 40° C. are preferred. The reaction is carried out until precipitation is complete, usually within one hour.

After the reaction is complete, the solid immonium complex is isolated, as by filtration, and washed with solvent, preferably the same as used in the initial solution. Then, the E ketoxime isomer immonium complex is neutralized to obtain the free E ketoxime. Neutralization is readily carried out using dilute aqueous solutions of alkali metal salts, particularly Na and K, of weakly ionized organic acids, such as carbonic acid and oxalic acid, e.g., sodium carbonate, potassium carbonate, sodium bicarbonate, sodium oxalate, and potassium oxalate. In general, the concentration of the aqueous solution can be between about 10 weight percent and about 15 weight percent and usually about 10 weight percent. A large excess of the aqueous solution is used, in the order of about 3 parts per part immonium complex.

The aryl alkyl ketoximes are prepared from aryl alkyl ketones and excess hydroxylamine hydrochloride in the presence of a base, in a manner familiar to those skilled in the art. In practice, the aryl alkyl ketoximes usually are obtained as a mixture of E and Z isomers. The ketoximes are precursors for preparing active insecticides by converting them to ketoximinoethers for example, by reacting the sodium ketoximate with substituted alkyl bromides, such as m-phenoxybenzylbromide. These insecticidal compounds have the general structure:

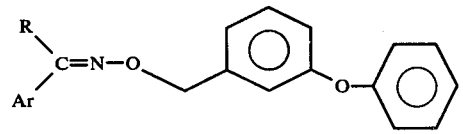

Because of the oximino function, the existence of both E and Z geometrical isomers of the ketoximinoethers is possible. Indeed, a mixture of both isomers is obtained when the starting ketoxime is itself a mixture of geometrical isomers. It has been found, however, that the overall insecticidal activity of the E isomer of the ketoximinoether is superior to that of the Z isomer. It has also been found that the E isomer of the ketoxime can be converted to the E isomer of the ketoximinoether with complete retention of stereochemistry. Accordingly, the process of this invention to convert mixtures of E and Z isomers of the ketoxime to the E isomer is highly desirable and significant.

The following examples demonstrate the process of this invention and the conversion of the resultant E ketoximes to the oximinoethers. In the Examples the ketoxime ratios are ascertained using two corroborative methods: (1) comparison of the E/Z isomer ratio of the thermally stable trimethyl silyl derivative of the oxime before and after acid (HCl) treatment, by gas chromatograph analysis and (2) comparison of the relative integration in the H$^1$ NMR of the separate resonances for the E and Z isopropyl methine protons, before and after the acid (HCl) treatment. The E stereochemistry was concluded from both H$^1$ and C$^{13}$ chemical shift data. References: J. Am. Chem. Soc. 86, 4373 (1964); Tet. 23, 1079–1095 (1967); J. Am. Chem. Soc. 94, 4897 (1972); J.O.C. 39(8), 1017 (1974).

EXAMPLE 1

A 60:40 E/Z isomeric mixture of p-chloroisobutyrophenone oxime (151 g., 0.76 m) was dissolved in 500 ml of anhydrous diethyl ether. The solution was saturated with anhydrous HCl, whereupon a voluminous amount of pure E oxime hydrochloride precipitated. The solid was filtered and washed well with dry ether. The dried hydrochloride salt was then added in portions to a vigorously stirring solution of 2500 ml. of 10% $Na_2CO_3$. The free oxime was filtered, washed with $H_2O$ until washings were neutral, and dried, under reduced pressure to yield 145 g. of 98% E p-chlorophenyl isopropyl ketoxime.

EXAMPLE 2

A 50:50 isomeric mixture of p-bromosiobutyrophenone oxime was isomerized to >98% E oxime via the procedure of Example 1.

EXAMPLE 3

An 80:20 E/Z isomeric mixture of 3-methyl, 4-ethoxyisobutyrophenone oxime was isomerized to >98% E oxime via the procedure of Example 1.

EXAMPLE 4

A 50:50 E/Z isomeric mixture of 3,4 indanyl, isopropyl ketoxime was isomerized to >98% E oxime via the procedure of Example 1.

EXAMPLE 5

A 70:30 E/Z mixture of p-chlorophenyl cyclopropyl ketoxime was isomerized to >98% E isomer via the procedure of Example 1.

Example 6 is a typical illustration of a stereospecific synthesis of an insecticidally active ketoximinoether using the E oxime of Example 1.

EXAMPLE 6

A solution of 0.02 mole of >98% E p-chloroisobutyrophenone oxime in 20 ml. of ethanol was added to a freshly prepared ethanolic solution of 0.02 mole NaOEt. The mixture was stirred at room temperature for 30 minutes and concentrated under reduced pressure to dryness. The resulting sodium oximate salt was dissolved in a minimum volume of DMF, whereupon 0.02 mole of m-phenoxybenzyl bromide was added dropwise, causing an exotherm of ~8°. The reaction mixture was stirred overnight at room temperature and poured into $H_2O$. The resulting oil was extracted two times into toluene. The combined organic layers were washed twice with $H_2O$, dried over $MgSO_4$, and concentrated under reduced pressure to yield 0.019 mole of >98% E-1-(4-chlorophenyl)-2-methyl 1-propanone, 0-(3-phenoxyphenyl) methyl oxime.

EXAMPLE 7

The >98% E isomer of 1-(4-bromophenyl)-2-methyl 1-propanone, 0-(3-phenoxyphenyl) methyl oxime was prepared via the procedure of Example 6.

EXAMPLE 8

The >98% E isomer of 1-(3-methyl, 4-ethoxyphenyl)-2-methyl 1-propanone, 0-(3-phenoxyphenyl) methyl oxime was prepared via the procedure of Example 6.

EXAMPLE 9

The >98% E isomer of 1-(2,3-dihydro-1H-indenyl 5-yl)-2-methyl-1-propanone, 0-(3-phenoxyphenyl) methyl oxime was prepared via the procedure of Example 6.

EXAMPLE 10

The 98% E isomer of cyclopropyl (p-chlorophenyl) methanone, 0-(3-phenoxyphenyl) methyl oxime was prepared via the procedure of Example 6.

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the appended claims.

What is claimed is:

1. A process for producing >98% pure E isomer of an aryl alkyl ketoxime having the formula:

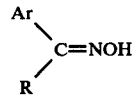

wherein Ar is phenyl; phenyl substituted in the 2- to 6-position with 1-5 halogen (Cl, Br, F, I), $C_1$–$C_4$ alkyl, $C_1$–$C_4$ alkoxy, $C_1$–$C_4$ alkylthio, methylenedioxy, ethylenedioxy, isopropylenedioxy, trifluoromethyl, $C_1$–$C_4$ haloalkyl, $C_1$–$C_4$ alkylthioalkyl, $C_2$–$C_4$ alkenyl, $C_2$–$C_4$ alkynyl, cyano, $C_2$–$C_4$ cyanoalkyl, $C_2$–$C_4$ carboalkoxy, $C_1$–$C_4$ alkylsulfonyl, $C_2$–$C_8$ alkoxyalkyl, $C_2$–$C_4$ haloalkenyl, or $C_1$–$C_4$ acyl; indanyl; naphthyl; benzofuryl; benzodihydrofuryl; benzothienyl; thienyl; R is $C_2$–$C_6$ alkyl, $C_3$–$C_6$ cycloalkyl, or $C_2$–$C_6$ alkenyl, any of which can be substituted by halogen, hydroxy, $C_1$–$C_4$ alkoxy, $C_1$–$C_4$ alkylsulfonyl, cyano, nitro, $C_2$–$C_4$ carboalkoxy, or $C_1$–$C_4$ acyl; that comprises contacting a solution of mixed E and Z isomers of said aryl alkyl ketoxime in an anhydrous organic solvent with at least a stoichiometric amount of anhydrous protic or Lewis acid at between about $-20°$ C. and about 150° C., thereby precipitating the E isomer of an immonium complex of said aryl alkyl ketoxime, separating said precipitate, neutralizing said precipitate with an excess of dilute aqueous $Na_2CO_3$ or $NaHCO_3$, and separating said E isomer.

2. The process of claim 1, wherein the solvent is anhydrous diethyl ether, the temperature is between about 10° C. and about 40° C. and the protic acid is anhydrous HCl.

3. The process of claim 2, wherein Ar is p-chlorophenyl and R is isopropyl.

4. The process of claim 2, wherein Ar is p-bromophenyl and R is isopropyl.

5. The process of claim 2, wherein Ar is 3-methyl-4-ethoxyphenyl and R is isopropyl.

6. The process of claim 2, wherein Ar is 3,4-indanyl and R is isopropyl.

7. The process of claim 2, wherein Ar is p-chlorophenyl and R is cyclopropyl.

* * * * *